(12) United States Patent
Ortiz et al.

(10) Patent No.: US 8,221,438 B2
(45) Date of Patent: Jul. 17, 2012

(54) LUMEN REDUCTION METHODS AND DEVICES

(75) Inventors: Mark S. Ortiz, Milford, OH (US); Michael J. Stokes, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1649 days.

(21) Appl. No.: 11/307,698

(22) Filed: Feb. 17, 2006

(65) Prior Publication Data
US 2007/0198034 A1 Aug. 23, 2007

(51) Int. Cl.
*A61B 17/12* (2006.01)
(52) U.S. Cl. ........................................ 606/142; 606/139
(58) Field of Classification Search ................ 606/142, 606/74, 75, 103, 139, 143, 151, 152, 153, 606/219, 232; 227/175.1–182.1
See application file for complete search history.

(56) References Cited

U.S. PATENT DOCUMENTS

| | | | |
|---|---|---|---|
| 2,004,013 A | 6/1935 | Reed | |
| 2,004,014 A | 6/1935 | Sanford | |
| 2,004,172 A | 6/1935 | Niday | |
| 4,841,888 A | 6/1989 | Mills et al. | |
| 4,899,744 A * | 2/1990 | Fujitsuka et al. | 606/153 |
| 5,041,129 A | 8/1991 | Hayhurst et al. | |
| 5,080,663 A | 1/1992 | Mills et al. | |
| 5,217,486 A | 6/1993 | Rice et al. | |
| 5,242,457 A * | 9/1993 | Akopov et al. | 606/144 |
| 5,269,809 A | 12/1993 | Hayhurst et al. | |
| 5,376,101 A | 12/1994 | Green et al. | |
| 5,395,030 A * | 3/1995 | Kuramoto et al. | 227/179.1 |
| 5,398,670 A | 3/1995 | Ortiz et al. | |
| 5,437,681 A | 8/1995 | Meade et al. | |
| 5,462,558 A | 10/1995 | Kolesa et al. | |
| 5,507,754 A * | 4/1996 | Green et al. | 606/139 |
| 5,514,159 A | 5/1996 | Matula et al. | |
| 5,540,705 A | 7/1996 | Meade et al. | |
| 5,571,119 A | 11/1996 | Atala | |
| 5,584,861 A | 12/1996 | Swain et al. | |
| 5,707,380 A * | 1/1998 | Hinchliffe et al. | 606/153 |
| 5,709,693 A | 1/1998 | Taylor | |

(Continued)

FOREIGN PATENT DOCUMENTS
EP 0641546 A1 3/1995
(Continued)

OTHER PUBLICATIONS
Partial EP Search Report, Appl. No. 07250668.6, dated Jun. 5, 2007, 6 pp.

*Primary Examiner* — Corrine M McDermott
*Assistant Examiner* — Gregory Anderson
(74) *Attorney, Agent, or Firm* — Nutter McClennen & Fish LLP

(57) ABSTRACT

Devices and methods for reducing a size of a lumen are provided. In one embodiment, a lumen reduction device is provided having an end effector with a trough formed therein for receiving tissue surrounding a lumen, and a plurality of fasteners configured to engage the tissue disposed within the trough. In use, the end effector can be actuated to deliver the fasteners to the tissue, and one or more sutures coupled to the fasteners can be used to pull the fasteners together and thereby cinch the tissue to reduce the size of a lumen.

26 Claims, 6 Drawing Sheets

U.S. PATENT DOCUMENTS

| | | | |
|---|---|---|---|
| 5,713,910 A | 2/1998 | Gordon et al. | |
| 5,755,730 A | 5/1998 | Swain et al. | |
| 5,807,393 A * | 9/1998 | Williamson et al. | 606/32 |
| 5,814,071 A | 9/1998 | McDevitt et al. | |
| 5,860,992 A | 1/1999 | Daniel et al. | |
| 5,887,594 A | 3/1999 | LoCicero, III | |
| 5,899,921 A | 5/1999 | Caspari et al. | |
| 5,902,321 A | 5/1999 | Caspari et al. | |
| 6,010,515 A | 1/2000 | Swain et al. | |
| 6,036,694 A | 3/2000 | Goble et al. | |
| 6,193,734 B1 | 2/2001 | Bolduc et al. | |
| 6,200,329 B1 | 3/2001 | Fung et al. | |
| 6,254,642 B1 | 7/2001 | Taylor | |
| 6,346,111 B1 | 2/2002 | Gordon et al. | |
| 6,358,259 B1 | 3/2002 | Swain et al. | |
| 6,443,962 B1 | 9/2002 | Gaber | |
| 6,454,778 B2 | 9/2002 | Kortenbach | |
| 6,494,888 B1 | 12/2002 | Laufer et al. | |
| 6,500,195 B2 | 12/2002 | Bonutti | |
| 6,506,196 B1 | 1/2003 | Laufer | |
| 6,524,328 B2 | 2/2003 | Levinson | |
| 6,540,789 B1 | 4/2003 | Silverman et al. | |
| 6,558,400 B2 | 5/2003 | Deem et al. | |
| 6,572,629 B2 | 6/2003 | Kalloo et al. | |
| 6,663,639 B1 | 12/2003 | Laufer et al. | |
| 6,719,763 B2 | 4/2004 | Chung et al. | |
| 6,746,460 B2 | 6/2004 | Gannoe et al. | |
| 6,755,843 B2 | 6/2004 | Chung et al. | |
| 6,773,440 B2 | 8/2004 | Gannoe et al. | |
| 6,773,441 B1 | 8/2004 | Laufer et al. | |
| 6,821,858 B2 | 11/2004 | Namatame et al. | |
| 6,835,200 B2 | 12/2004 | Laufer et al. | |
| 6,869,395 B2 | 3/2005 | Page et al. | |
| 6,908,427 B2 | 6/2005 | Fleener et al. | |
| 6,955,643 B2 | 10/2005 | Gellman et al. | |
| 7,588,582 B2 * | 9/2009 | Starksen et al. | 606/139 |
| 2001/0023352 A1 | 9/2001 | Gordon et al. | |
| 2002/0107530 A1 | 8/2002 | Sauer et al. | |
| 2002/0193809 A1 | 12/2002 | Meade et al. | |
| 2003/0032967 A1 | 2/2003 | Park et al. | |
| 2003/0083674 A1 | 5/2003 | Gibbens | |
| 2003/0109900 A1 | 6/2003 | Martinek | |
| 2003/0120265 A1 | 6/2003 | Deem et al. | |
| 2003/0120292 A1 | 6/2003 | Park et al. | |
| 2003/0171760 A1 | 9/2003 | Gambale | |
| 2003/0181924 A1 | 9/2003 | Yamamoto et al. | |
| 2003/0225312 A1 | 12/2003 | Suzuki et al. | |
| 2003/0229296 A1 | 12/2003 | Ishikawa et al. | |
| 2003/0233104 A1 | 12/2003 | Gellman et al. | |
| 2003/0233108 A1 | 12/2003 | Gellman et al. | |
| 2004/0002720 A1 | 1/2004 | Kortenbach et al. | |
| 2004/0006351 A1 | 1/2004 | Gannoe et al. | |
| 2004/0024386 A1 | 2/2004 | Deem et al. | |
| 2004/0034369 A1 | 2/2004 | Sauer et al. | |
| 2004/0059350 A1 | 3/2004 | Gordon et al. | |
| 2004/0082963 A1 * | 4/2004 | Gannoe et al. | 606/153 |
| 2004/0098050 A1 | 5/2004 | Foerster et al. | |
| 2004/0122452 A1 | 6/2004 | Deem et al. | |
| 2004/0122453 A1 | 6/2004 | Deem et al. | |
| 2004/0122456 A1 | 6/2004 | Saadat et al. | |
| 2004/0122473 A1 | 6/2004 | Ewers et al. | |
| 2004/0147958 A1 | 7/2004 | Lam et al. | |
| 2004/0162568 A1 | 8/2004 | Saadat et al. | |
| 2004/0193184 A1 | 9/2004 | Laufer et al. | |
| 2004/0194790 A1 | 10/2004 | Laufer et al. | |
| 2004/0210243 A1 | 10/2004 | Gannoe et al. | |
| 2004/0215058 A1 | 10/2004 | Zirps et al. | |
| 2005/0015101 A1 | 1/2005 | Gibbens et al. | |
| 2005/0033319 A1 | 2/2005 | Gambale et al. | |
| 2005/0055038 A1 | 3/2005 | Kelleher et al. | |
| 2005/0070921 A1 | 3/2005 | Ortiz et al. | |
| 2005/0070926 A1 | 3/2005 | Ortiz | |
| 2005/0070931 A1 | 3/2005 | Li et al. | |
| 2005/0070934 A1 | 3/2005 | Tanaka et al. | |
| 2005/0070935 A1 | 3/2005 | Ortiz | |
| 2005/0075653 A1 | 4/2005 | Saadat et al. | |
| 2005/0075654 A1 | 4/2005 | Kelleher | |
| 2005/0119542 A1 | 6/2005 | Stoddart et al. | |
| 2005/0143760 A1 | 6/2005 | Imran | |
| 2005/0143762 A1 | 6/2005 | Paraschac et al. | |
| 2005/0149067 A1 | 7/2005 | Takemoto et al. | |
| 2005/0165419 A1 | 7/2005 | Sauer et al. | |
| 2005/0192599 A1 | 9/2005 | Demarais | |
| 2005/0192601 A1 | 9/2005 | Demarais | |
| 2005/0203488 A1 | 9/2005 | Michlitsch et al. | |
| 2005/0228415 A1 | 10/2005 | Gertner | |
| 2005/0273138 A1 * | 12/2005 | To et al. | 606/219 |
| 2006/0020277 A1 | 1/2006 | Gostout et al. | |

FOREIGN PATENT DOCUMENTS

| | | |
|---|---|---|
| EP | 1447052 A2 | 8/2004 |
| WO | WO-95/19140 | 7/1995 |
| WO | WO-00/61012 | 10/2000 |
| WO | WO-01/10312 | 2/2001 |
| WO | WO-01/66001 | 9/2001 |
| WO | WO-01/89393 | 11/2001 |
| WO | WO-02/096327 | 12/2002 |
| WO | WO-2004/021894 | 3/2004 |
| WO | WO-2005/034729 | 4/2005 |

* cited by examiner

LUMEN REDUCTION METHODS AND DEVICES

FIELD OF THE INVENTION

The present invention relates to devices and methods for bariatric surgery, and in particular, to devices and methods for reducing the size of a lumen.

BACKGROUND OF THE INVENTION

One treatment for morbid obesity is bariatric surgery which involves alteration of a patient's digestive tract to encourage weight loss and to help maintain a normal weight. A common type of bariatric surgery is gastric bypass surgery, which aims to decrease the size of a patient's stomach by dividing it into upper and lower pouches using staples and/or stitches. The jejunum (the middle section of the small intestine) is also divided into two parts. One part of the jejunum, called the "Roux limb," is brought up behind the colon and lower stomach pouch, and joined or "anastamosed" to the upper stomach pouch. The remaining end of the jejunum is attached to the side of the Roux limb. As a result, a new digestive pathway is created through which food travels down the esophagus, into the upper stomach pouch, and through the anastomosis (or stoma) into the Roux limb. Digestive juices from the stomach, the liver, and the pancreas travel through the lower stomach pouch, down the duodenum and jejunum, and into the Roux limb where the two parts of the jejunum are attached and further digestion takes place.

While effective, gastric bypass surgery is not without complications. For example, the stoma may dilate over time, allowing a patient to eat more and causing them to gain weight. Accordingly, there remains a need for improved devices and methods for bariatric surgery, and in particular, for devices and methods for reducing the size of a stoma.

BRIEF SUMMARY OF THE INVENTION

The present invention provides various devices and methods for reducing a size of a lumen. In one embodiment, a lumen reduction device is provided having an end effector with a trough formed therein for receiving tissue around a lumen, and several fasteners releasably disposed therein. The fasteners can be positioned in a substantially circumferential pattern, and can engage tissue disposed within the trough. The device can also include at least one suture coupled to at least two of the fasteners and configured to be cinched to pull the fasteners together to reduce a size of a lumen. By way of non-limiting example, the device can include a first suture coupled to at least two fasteners, and a second suture coupled to at least two fasteners different from the fasteners coupled to the first suture.

The end effector can have a variety of configurations, but it is preferably adapted to be positioned within a lumen. In one embodiment, the end effector can have proximal and distal housing portions that define the trough therebetween. In an exemplary embodiment, the trough is formed around the circumference of the end effector. The trough can have a fixed size or alternatively it can have an adjustable size. For example, the proximal and distal housing portions can be movable to allow adjustment of the size of the trough. The trough can include features for gathering tissue, and in one embodiment the trough can include at least one suction port for suctioning tissue into the trough. In an exemplary embodiment, a plurality of suction ports are formed within the trough around the entire circumference thereof.

The trough can also optionally include features for injuring the tissue such that it bleeds. The tissue-injuring elements can be located at a variety of locations in the trough, but in an exemplary embodiment the tissue-injuring elements are disposed on opposed walls of the trough such that tissue within the trough can be positioned between the tissue-injuring elements. A variety of electrical and mechanical elements can be used as tissue-injuring elements, such as RF electrodes, monopolar electrodes, bipolar electrodes, mechanical scrapers, and combinations thereof.

The end effector can also be adapted to hold fasteners that can be applied to tissue disposed within the trough. While a variety of fastener holding techniques can be used, in one embodiment the trough can include channels formed therein. The shape and the size of the channels can vary depending upon the type of fasteners used. In one embodiment, the fasteners can have an elongate shape in an open position, and a ring-shape in a closed position. The fasteners can be biased to the closed position in which they are effective to engage tissue. The channels in the trough can be longitudinal cut-outs that extend between the proximal and distal housings to allow the fastener to extend across the trough. The fasteners can be held within the channel using a variety techniques, and in one embodiment the device can include proximal and distal fastener-retaining members located within the proximal and distal housings. The fastener-retaining members can have a variety of configurations depending upon the type of fastener used, however in one embodiment, the proximal fastener-retaining member is adapted to retain a first end of the fasteners, and the distal fastener-retaining member is adapted to retain a second, opposed end of the fasteners. In an exemplary embodiment, the proximal and distal fastener-retaining members are adapted to rotate to release the first and second ends of the fasteners into tissue. Rotation of the proximal and distal fastener-retaining members can be affected, for example, by first and second rotatable actuators that are coupled to the proximal and distal fastener-retaining members, respectively. The first and second actuators can be configured to be independently rotated, or alternatively, the first and second actuators can be rotated simultaneously. In other embodiments, the proximal and distal fastener-retaining members can be configured to release each fastener individually. For example, the legs of the fastener-retaining members can vary in length, such that the fastener-retaining members will release the fasteners sequentially as the fastener-retaining members are rotated.

Methods for reducing a size of a lumen are also provided. In one embodiment, a method can include positioning an end effector having a trough for receiving tissue within a lumen, actuating the end effector to deliver fasteners positioned within a substantially circumferential pattern around the end effector into the tissue, and cinching at least one suture coupled to at least two of the fasteners to pull the fasteners together and thereby reduce the size of the lumen. In one exemplary embodiment, actuation of the end effector can cause at least a portion of one or more of the fasteners to be simultaneously applied to tissue. For example, a first end of the fasteners can be released from a proximal fastener-retaining member formed within a proximal housing of the end effector, and a second end of the fasteners can be released from a distal fastener-retaining member formed within a distal housing of the end effector. The first end of the fasteners can be released independently from the second end of the fasteners. The method can also include suctioning tissue surrounding the end effector into the trough, as well as activating the end effector to injure tissue. While a variety of activation techniques can be used, in one embodiment, energy can be delivered to one or more tissue-injuring elements disposed within the trough to cause the tissue to bleed. In general, one or more portions of the device can be reconditioned after at least one use of the device. Such reconditioning can include replacing or cleaning at least a portion of any one of the pieces of the device, as well as optionally disassembling or reassembling the device.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides devices and methods for reducing a size of a lumen. In general, the device can include an end effector having a trough formed therein for receiving tissue, and for delivering a plurality of fasteners to the tissue. The fasteners can be coupled by one or more sutures which can be used to cinch the tissue and thereby reduce the size of the lumen. The device can also include features to facilitate engagement of tissue within the trough, injury of tissue to promote healing, and various other features to facilitate use of the device. A person skilled in the art will appreciate that the present device can be used in any procedure where it is necessary to apply fasteners and/or reduce the size of a lumen, such as stoma, jejunum, duodenum, or colon reduction procedures.

Figure 1:
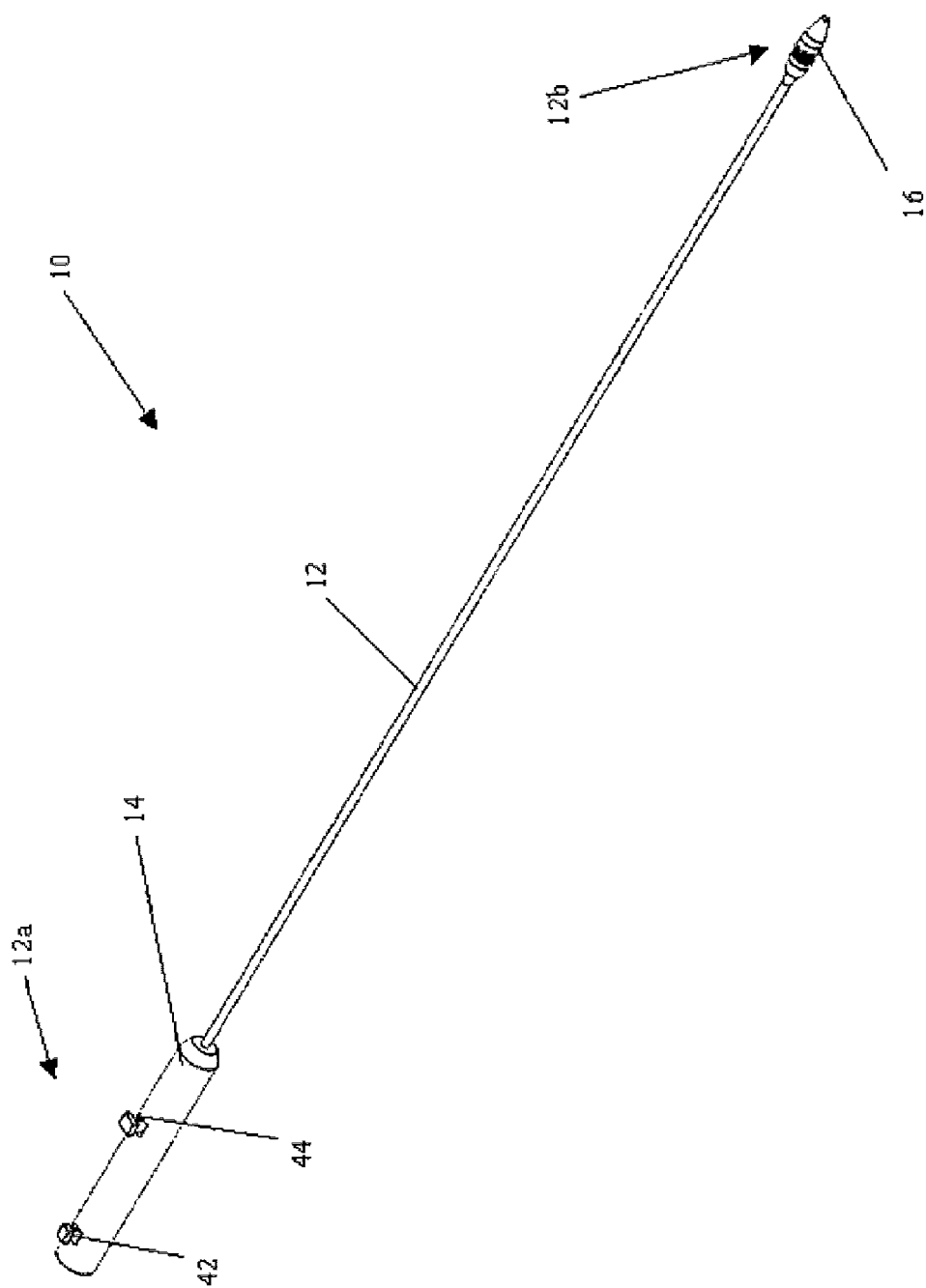
FIG. 1 is perspective view of one embodiment of a lumen reduction device.

FIG. 1 illustrates one exemplary embodiment of a lumen reduction device 10 for reducing the size of a lumen. In general, the device 10 includes an outer shaft 12 having proximal and distal ends 12a, 12b. The outer shaft 12 can have virtually any configuration, and it can be flexible or rigid. In an exemplary embodiment, the outer shaft 12 has a configuration that allows it to be endoscopically inserted through the esophagus. The proximal end 12a can include a handle 14 and the distal end 12b can include an end effector 16 for receiving and treating tissue.

Figure 2A:
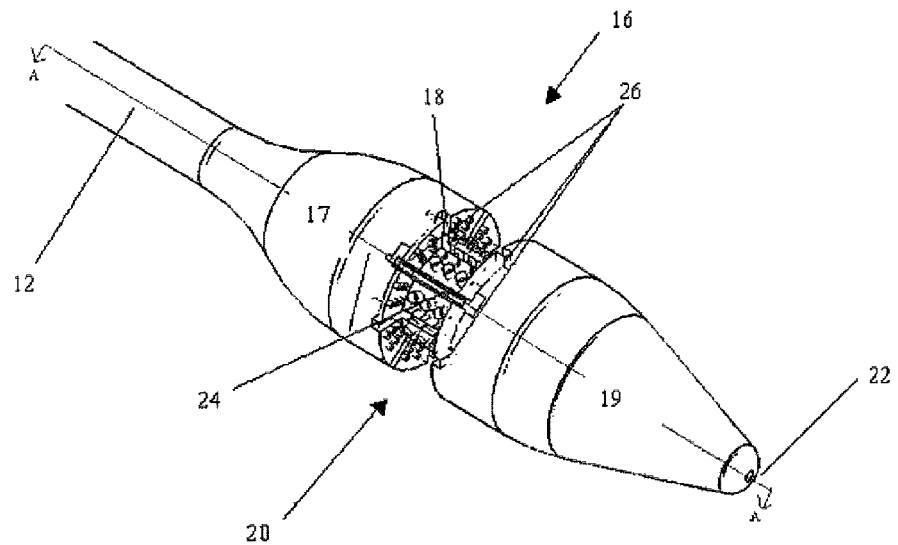
FIG. 2A is a perspective view of an end effector of the device of FIG. 1.
Figure 2B:
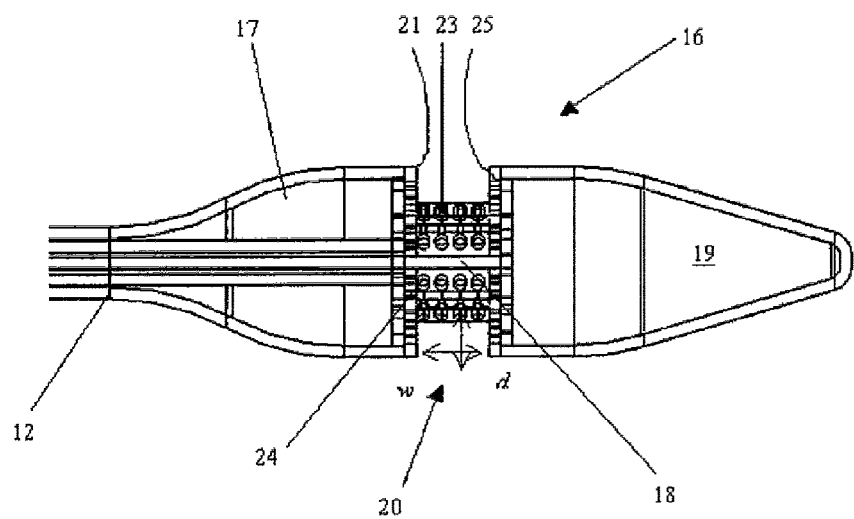
FIG. 2B is a cross-sectional view of the end effector of FIG. 2A taken across line A-A, showing the proximal and distal housing portions and the trough of the end effector.

The end effector 16 is shown in more detail in FIGS. 2A-2B. While the shape of the end effector can vary, it is preferably shaped to be positioned within a lumen, and includes a trough for holding tissue. The end effector 16 is also preferably adapted to releasably retain one or more fasteners for delivering the fasteners to tissue disposed within the trough. In the illustrated embodiment, the end effector 16 includes proximal and distal housing portions 17, 19 that are connected by a connector portion 18, and that define the trough 20 therebetween. The housing portions 17, 19 can be integrally formed with one another and/or the outer shaft 12, or they can be separate from one another and/or the outer shaft 12. While the housing portions 17, 19 can have a variety of configurations, in the embodiment shown in FIG. 2B each housing portion 17, 19 has a substantially cylindrical, hollow configuration for retaining one or more fasteners therein, as will be discussed in more detail below. The connector portion 18 can have a diameter smaller than a diameter of the proximal and distal housing portions 17, 19 to define the trough 20 therebetween. The housing portions 17, 19 can also include features to facilitate insertion into the esophagus. By way of non-limiting example, the distal housing portion 19 can include a tapered end with a blunt tip. The proximal and distal housing portions 17, 19 can also optionally include a lumen 22 formed therethrough for receiving a guidewire to facilitate positioning of the device within a lumen.

The trough 20 formed between the proximal and distal housing portions 17, 19 can be located at a variety of locations on the end effector 16, and it can extend partially or entirely around a circumference thereof. In an exemplary embodiment, the trough 20 is formed around the entire circumference of the end effector 16 to allow tissue surrounding a lumen to be received therein. The trough 20 can have any shape and size depending upon the amount of tissue to be received. In the illustrated embodiment, the trough 20 has a substantially rectangular cross-sectional shape with a backwall 21 that is defined by the connector 18, and opposed endwalls 23, 25 that are defined by the proximal and distal housing portions 17, 19. The size of the trough 20 should be sufficient to receive the amount of tissue to be fastened. In an exemplary embodiment, the trough 20 has a depth d of at least about 3 mm and a width w of at least about 5 mm. The trough 20 can also optionally have an adjustable size. For example, one or both of the proximal and distal housing portions 17, 19 can be movably coupled to the connector 18 to allow the housing portions 17, 19 to slide relative to one another and thereby increase or decrease the width w of the trough 20. A lever located on the connector 18 can optionally be provided for controlling and adjusting the size of the trough.

As explained above, the trough 20 is configured to receive tissue. While a variety of techniques can be used to position tissue within the trough 20, in one embodiment the trough 20 can include a plurality of suction elements 24 for suctioning tissue therein. The trough 20 can include any number of suction elements 24, and each suction element 24 can have any shape, such as ports or slots, and can have any size. The suction elements 24 can also be formed anywhere on the trough 20. As shown in FIG. 2B, the trough 20 includes suction ports 24 that are located around the entire circumference of the trough 20, that is, on the basewall 21 and the endwalls 23, 25. The suction ports 24 can also be positioned in any pattern that is effective for engaging tissue, such as in equally spaced rows within the trough 20. In use, a suction force can be generated using a pump or other element coupled to the proximal end of the shaft or the handle to pull air into the ports and suction the tissue therein.

The trough 20 can also optionally be adapted to injure or cause intentional injury to tissue, thereby promoting healing when the tissue is cinched together. Any tissue-injuring technique can be used, and one or more tissue-injuring elements can be positioned anywhere within the trough 20. In an exemplary embodiment, one or more tissue-injuring elements are positioned on the opposed endwalls 23, 25 of the trough 20. The tissue-injuring elements can also be located around the entire circumference of the trough 20 and spaced a distance apart from one another or located only in zones that are being cinched. The tissue-injuring elements can be in the form of electrical elements, such as electrodes for delivering RF, monopolar, bipolar, or other energy to the tissue, or mechanical elements, such as scrapers or little blades located on the endwalls of the trough that move to cut the tissue. In an exemplary embodiment, the tissue-injuring elements are in the form of two bipolar or monopolar strips that are disposed on the opposed endwalls 23, 25 and around the circumference of the trough 20. Alternatively, a portion of each endwall 23, 25 can be formed from a conductive material for receiving energy. The location of the tissue-injuring elements on the endwalls 23, 25 allows the applied energy to travel across or between the walls of the proximal and distal housing portions 17, 19 and through tissue 64 contained within the trough 20. Energy can be delivered to the strips through one or more leads extending through the housing and coupled to an internal or external energy source.

Figure 2C:
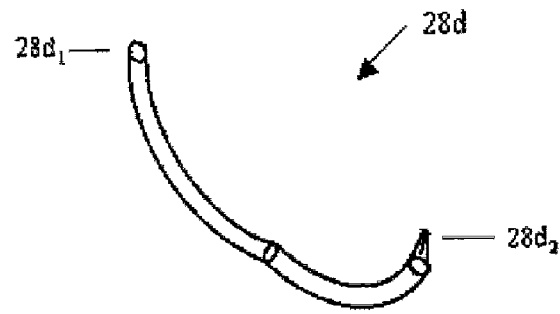
FIG. 2C is a perspective view of one embodiment of a fastener for use with the lumen reduction device of FIGS. 1-2B.

As also explained above, the end effector can be adapted to hold one or more fasteners for delivering the fasteners to tissue disposed within the trough. While a variety of techniques can be used to hold the fasteners in the end effector, in one embodiment, the trough 20 can include one or more channels 26 formed therein for seating the fasteners. The number and location of the channels 26 can vary depending upon the desired amount of tissue to be cinched. In the exemplary embodiment shown in FIG. 2A the channels 26 are disposed around the entire circumference of the trough 20 such that the fasteners are located in a circumferential pattern therearound. The shape and size of the channels can also vary depending upon the type of fasteners used, and various fasteners known in the art can be used. In an exemplary embodiment, the fasteners 28$d$ can have an elongate configuration with opposed ends 28$d_1$, 28$d_2$ that are adapted to penetrate tissue as shown in FIG. 2C, and the channels 26 have an elongate longitudinal configuration that extends through the sidewalls of the proximal and distal housing portions 17, 19, as well as the connector 18. The fasteners can be disposed within the channels 26 such that the fasteners extend across the channel 26, as will be discussed in more detail below. In an exemplary embodiment, the fasteners are biased to a closed, ring-shaped configuration, and the ends can be expanded to have an elongate configuration in an open position. The opposed ends of the fasteners can be held within the channels 26 in an open configuration using one or more fastener-retaining members, as will be discussed below. Upon release from the channels 26, the fasteners can close to form a ring-shaped member that engages the tissue. The fasteners can also include features to facilitate penetration of tissue, such as pointed ends and/or lubrication. FIG. 2C illustrates fastener 28$d$ having pointed end 28$d_2$. The size of each fastener can also vary depending upon the type and amount of tissue to be cinched. In an exemplary embodiment, the fasteners have a diameter that is about 3.5 mm in a closed position. A person skilled in the art will appreciate that the fasteners can be formed from a variety of biocompatible and superelastic materials, including, by way of non-limiting example, shape memory metals such as Nitinol.

Figure 3A:
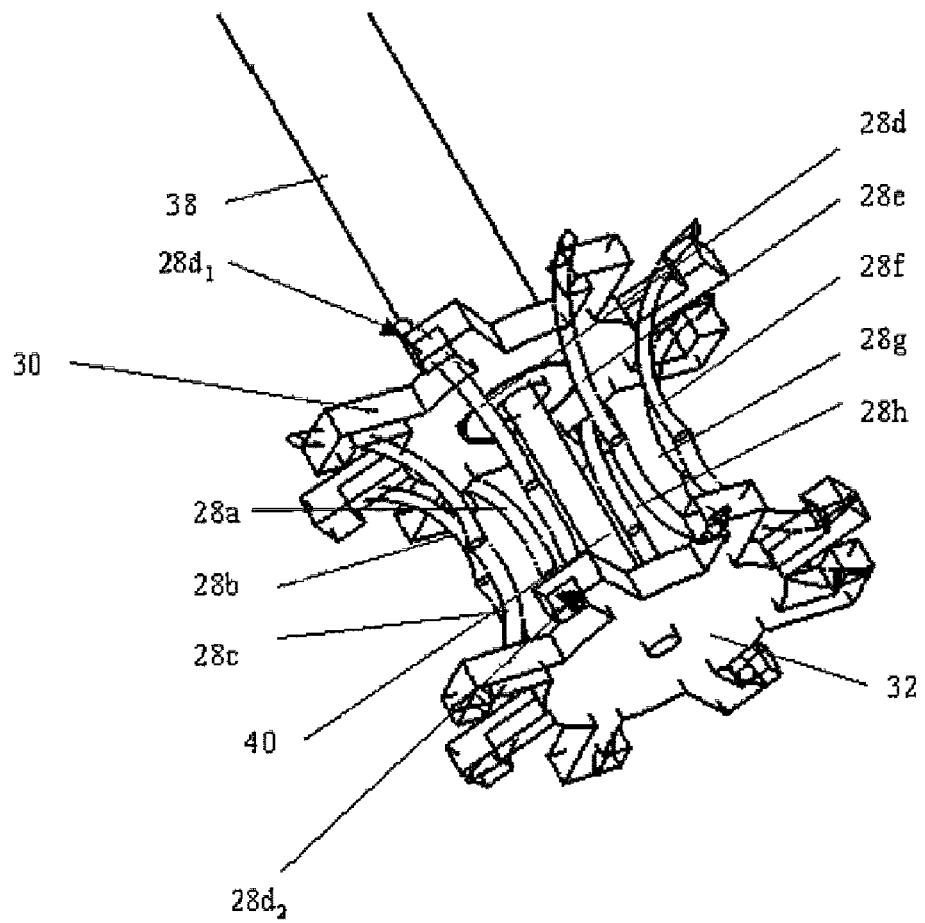
FIG. 3A is a perspective view of the actuators and fastener-retaining members of the end effector of FIG. 2B having a plurality of fasteners retained therein.
Figure 3B:
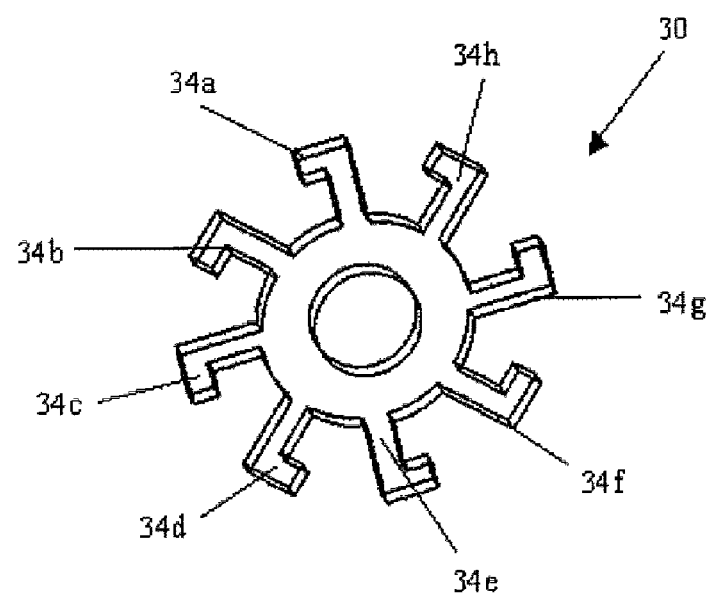
FIG. 3B is a front view of one of the fastener-retaining members of FIG. 3A.
Figure 3C:
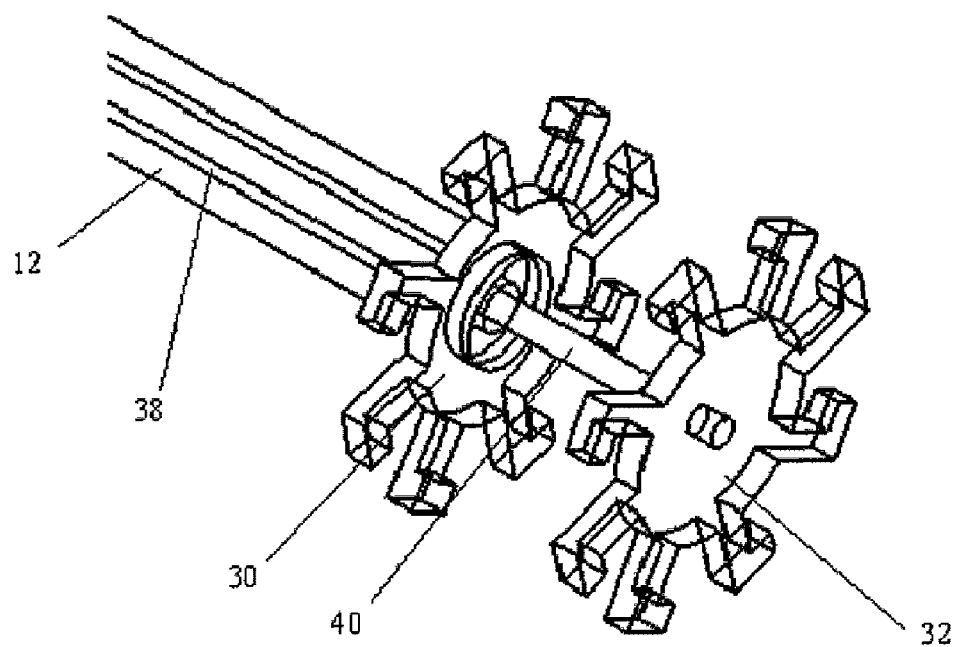
FIG. 3C is a transparent perspective view of the actuators and fastener-retaining members of the end effector of FIG. 2B.

As indicated above, the fasteners can be releasably retained within the channels using various techniques, but in an exemplary embodiment they are retained within the channels with proximal and distal fastener-retaining members that are disposed within the proximal and distal housings. FIG. 3B illustrates fastener-retaining member 30, which includes a central disc with several hook-shaped legs 34$a$, 34$b$, 34$c$, 34$d$, 34$e$, 34$f$, 34$g$, 34$h$ (hereinafter 34$a$-$h$) extending outwardly therefrom for holding the ends of the fasteners. As shown in FIG. 3A, the hook-shaped legs on the proximal fastener-retaining member 30 are adapted to hold the first end of the fastener (first end 28$d_1$ of fastener 28$d$ is shown) within the channels in the proximal housing portion 17, and the hook-shaped legs on the distal fastener-retaining member 32 are adapted to hold the second, opposed end of the fasteners (second end 28$d_2$ of fastener 28$d$ is shown) within the channels in the distal housing portion 19. The hook-shaped legs 34$a$-$h$ on each fastener-retaining member are preferably bent in the same direction and have substantially the same length to effect the simultaneous release of the legs of the fasteners, as will be discussed below. In other embodiments, as discussed above, each of the hook-shaped legs on each fastener-retaining member can have a different length to release the legs of the fasteners sequentially.

In use, the fastener-retaining members 30, 32 can be rotated to move the hook-shaped legs 34$a$-$h$ out of the channels, and thereby release the fasteners from the channels and into the tissue disposed in the trough. While a variety of techniques can be used to rotate the fastener-retaining members, in an exemplary embodiment, a first actuator 38 extends through the outer shaft 12 and is coupled to a midportion of the proximal fastener-retaining member 30, and a second actuator 40 extends through the first actuator 38 and the connector 18 and is coupled to a mid-portion of the distal fastener-retaining member 32. A proximal end of each actuator 38, 40 can include a lever 42, 44 formed thereon and slidably disposed within a slot formed in the handle 14. In use, the levers 42, 44 can be rotated within the slots in the handle 14 to rotate the first and second actuators 38, 40 simultaneously or independently of one another, thereby releasing the ends of the fasteners from the hook-shaped members, and allowing the fasteners to penetrate through and close around tissue disposed within the trough. In embodiments where the hook-shaped members have legs of varying lengths, rotation of the first and second actuators can cause the shortest leg of the fastener-retaining members to release the ends of the fastener held therein. Further rotation of the levers to effect rotation of the first and second actuators will release additional fasteners sequentially. The levers 42, 44 can optionally be biased, e.g. using a spring, to a first position to retain the ends of the fastener-retaining members within the channels, thereby retaining the ends of the fasteners in the channels and preventing accidental release of the fasteners. Alternatively the handle can include a locking mechanism for locking the levers in a first position. A person skilled in the art will appreciate that a dial, knob or any other mechanism can be used to trigger rotation of the first and second actuators. While rotatable actuation is shown, a person skilled in the art will also appreciate that a variety of other techniques can be used to effect movement of the fastener-retaining members 30, 32, and thereby release the ends of the fasteners.

Figure 4:
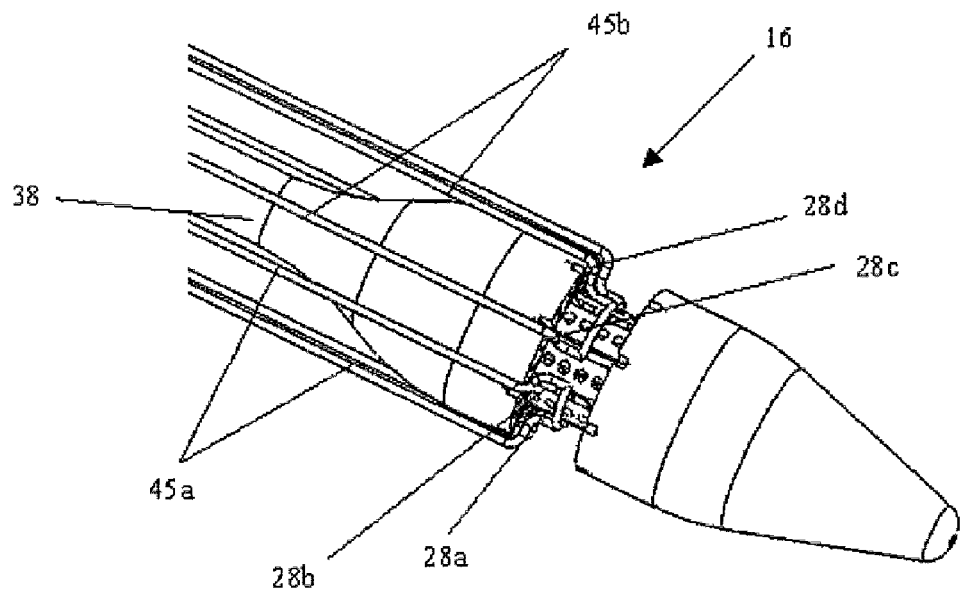
FIG. 4 is a partially cross-sectional view of the end effector of FIG. 1 having sutures coupled to fasteners contained therein.

The device can also be configured to hold one or more sutures to cinch the tissue engaged by the fasteners. FIG. 4 illustrates suture 45*a*, coupled to fasteners 28*a*, 28*b*, and suture 45*b* coupled to fasteners 28*c*, 28*d*. The sutures 45*a*, 45*b* extend across the fasteners 28*a*, 28*b*, 28*c*, 28*d* along the outside of the first actuator 38 and up through the outer shaft (not shown). Alternatively, the sutures can extend through the actuators or they can be positioned external to the device. The number of sutures can vary depending upon the amount of tissue to be cinched, and the sutures can be coupled to any number of fasteners. The sutures can also be located in predetermined zones, such that only a certain portion of the tissue surrounding a lumen is cinched. In use, when the fasteners are engaged with the tissue, the suture will extend through the ring-shaped fasteners, and the sutures can be pulled and tied to cinch the tissue.

Figure 5A:
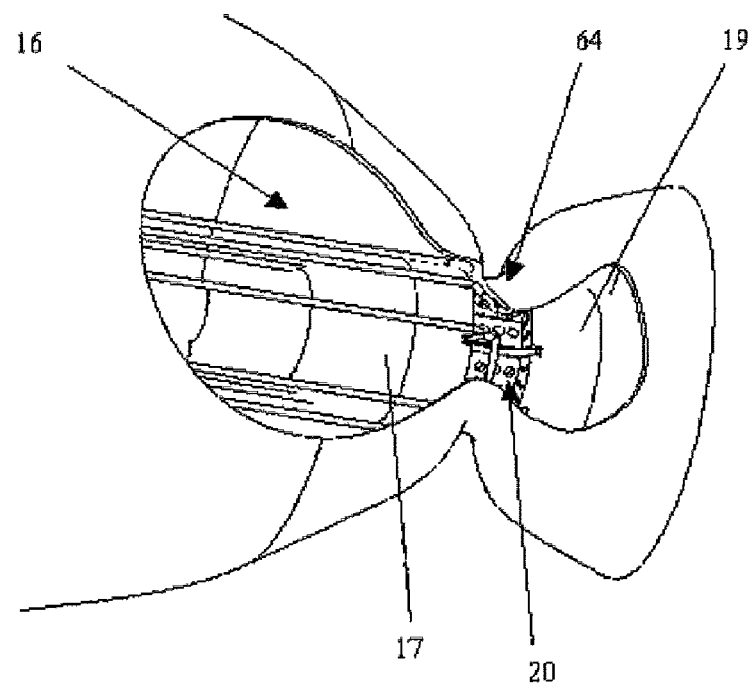
FIG. 5A is a partially cut-away side view of the end effector of FIG. 1 positioned within a stoma and suctioning tissue into a trough formed in the end effector.
Figure 5B:
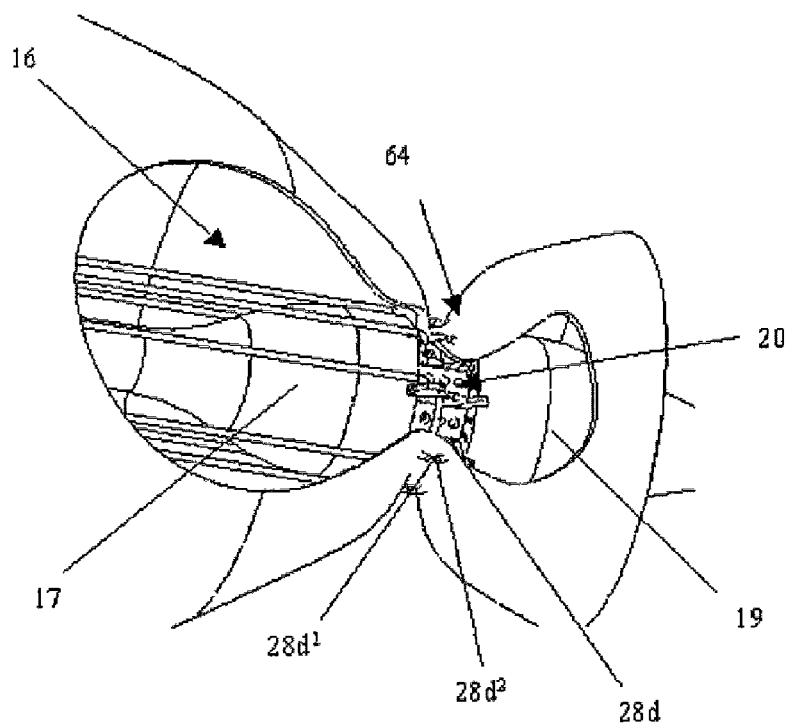
FIG. 5B is a partially cut-away side view of the end effector and stoma of FIG. 5A showing release of the fasteners from the fastener-retaining members.
Figure 5C:
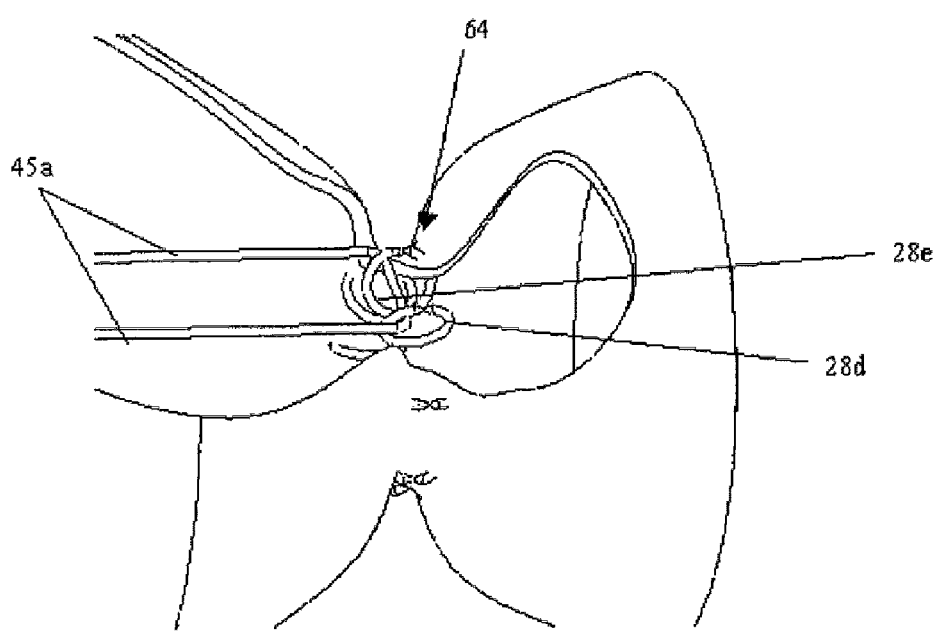
FIG. 5C is a partially cut-away side view of the stoma of FIG. 5B following removal of the end effector of FIG. 2A, and showing sutures extending through the fasteners for cinching tissue around the stoma.

FIGS. 5A-5C illustrate one embodiment of an exemplary method for reducing a size of a lumen, such as a stoma, using, by way of non-limiting example, the device of FIGS. 1-4. While a variety of techniques can be used to access the stoma, in an exemplary embodiment, the device can be inserted down the esophagus. A scope can optionally be used to facilitate positioning of the end effector. As the end effector 16 enters the stomach, the stomach can be insufflated to prevent collapse thereof and to allow for visibility of the stomach and stoma 64. The trough 20 can then be directed towards and positioned at the stoma 64. Once at the site of the stoma, suction can be applied to the tissue 64 using the suction ports to cause the tissue 64 to be suctioned into the trough 20, as shown in FIG. 5A, and the tissue-injuring elements can be activated to cause injury to the tissue 64 within the trough 20. Alternatively, in embodiments where the trough 20 does not include tissue-injuring elements, a device adapted to injure the tissue can be positioned at the tissue prior to the application of fasteners thereto from the end effector. In one embodiment, argon plasma coagulation can be used to injure the tissue, and a catheter having a controlled argon source and a high frequency electrical generator can be positioned at the tissue. The generator can then be activated, using an external energy source for example, such that current is delivered to the tissue and the tissue is injured.

Once the tissue 64 is injured, the fasteners can be applied thereto. In an exemplary embodiment as shown in FIG. 5B, the first actuator located within the proximal housing portion 17 is actuated by rotating the lever on the handle (shown in FIG. 1) to cause the proximal fastener-retaining member to rotate. As the proximal fastener-retaining member rotates, the first end of the fasteners (first end 28*d*$_1$ of fastener 28*d* is shown) are simultaneously released from the channels. The second actuator located within the distal housing portion 19 can then be actuated independently of the first actuator to rotate the distal fastener-retaining member. This can be achieved using the lever on the handle (shown in FIG. 1). As a result, the second end of the fasteners (second end 28*d*$_2$ of fastener 28*d* is shown) are simultaneously released from the channels. The ends will curve towards the first ends to form a ring-shaped fastener in the closed position. As noted above, the first and second actuators can optionally be actuated at the same time, causing both ends of the fasteners to be simultaneously released into tissue, and/or the fastener-retaining members can be adapted such that actuation of the actuators causes the release of a single fastener into tissue.

After the fasteners are released into the tissue, the stomach can optionally be insufflated again if necessary to separate the fasteners from the device to effect removal thereof. The device can be removed, leaving the fasteners (28*d*, 28*e* are shown) with the sutures (suture 45*a* is shown) extending therefrom, as shown in FIG. 5C. The trailing ends of each suture can be tensioned to pull the fasteners together, thereby causing the tissue to cinch to reduce the diameter of the stoma. The sutures can be tied or a fastening device, such as a knotting member, can be used to secure the ends of the sutures to one another. The free ends can then be cut off, or the knotting member can include a cutting element to cut the suture ends off.

Lumen reduction devices, including portions thereof, can be designed to be disposed after a single use, or can be designed to be used multiple times. In either case, however, the device can be reconditioned for reuse after at least one use. Reconditioning can include any combination of the steps of disassembly of the device, followed by cleaning or replacement of particular pieces, and subsequent reassembly. By way of example, the lumen reduction device of FIGS. 1-4 can be reconditioned after the device has been used in a medical procedure. The device can be disassembled, and any number of the particular pieces (e.g., the fasteners, actuators, end effector, tissue-injury elements, and sutures) can be selectively replaced or removed in any combination. For example, the fasteners and sutures can be replaced by adding a new fastener cartridge to the end effector or by replacing the proximal and distal fastener-retaining members with fully loaded fastener-retaining members and/or actuators. Upon cleaning and/or replacement of particular parts, the device can be reassembled for subsequent use either at a reconditioning facility, or by a surgical team immediately prior to a surgical procedure. Those skilled in the art will appreciate that reconditioning of a lumen reduction device can utilize a variety of techniques for disassembly, cleaning/replacement, and reassembly. Use of such techniques, and the resulting reconditioned lumen reduction device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A device for reducing a size of a lumen, comprising:
an end effector having a trough formed therein around a circumference thereof for receiving tissue around a lumen, and at least one suction port disposed within the trough and adapted to suction tissue therein;
a plurality of fasteners releasably disposed within the end effector and positioned in a substantially circumferential pattern, each of the plurality of fasteners having a proximal terminal end retained within a proximal portion of the trough, and a distal terminal end retained within a distal portion of the trough, and the plurality of fasteners being configured to engage tissue disposed within the trough; proximal and distal fastener-retaining members adapted to rotate to release the proximal and distal terminal ends of the plurality of fasteners to allow the plurality of fasteners to close and grasp tissue; and at least one suture coupled to at least two of the plurality of fasteners and configured to be cinched to pull at least two of the plurality of fasteners together and thereby reduce a size of a lumen.

2. The device of claim 1, further comprising at least one tissue-injuring element disposed within the trough and adapted to injure tissue.

3. The device of claim 2, wherein the trough includes a plurality of tissue-injuring elements spaced apart from one another in the trough.

4. The device of claim 3, wherein the plurality of tissue-injuring elements are disposed on opposed walls of the trough such that tissue disposed within the trough can be positioned between the plurality of tissue-injuring elements.

5. The device of claim 2, wherein the at least one tissue-injuring element is selected from the group consisting of RF electrodes, monopolar electrodes, bipolar electrodes, mechanical scrapers, and combinations thereof.

6. The device of claim 1, wherein the end effector includes proximal and distal housing portions spaced a distance apart from one another and defining the trough therebetween.

7. The device of claim 6, wherein the trough has a depth of at least about 3 mm and a width of at least about 5 mm.

8. The device of claim 6, wherein the proximal and distal housing portions are movable such that the trough has an adjustable size.

9. The device of claim 6, wherein the proximal fastener-retaining member is disposed within the proximal housing portion and the distal fastener-retaining member is disposed within the distal housing portion.

10. The device of claim 1, further comprising a first actuator coupled to the proximal fastener-retaining member and adapted to effect rotation of the proximal fastener-retaining member, and a second actuator coupled to the distal fastener-retaining member and adapted to effect the rotation of the distal fastener-retaining member.

11. The device of claim 10, wherein the first actuator is independently rotatable from the second actuator.

12. The device of claim 10, wherein the first and second actuators are configured to be simultaneously rotated.

13. The device of claim 1, wherein the proximal and distal fastener-retaining members are adapted to release the fasteners sequentially.

14. The device of claim 1, wherein the plurality of fasteners have an elongate shape in an open position, and a ring-shape in a closed position.

15. The device of claim 14, wherein the plurality of fasteners are biased to the closed position in which the plurality of fasteners are effective to engage tissue.

16. The device of claim 14, wherein the plurality of fasteners are formed from a shape memory material.

17. The device of claim 1, further comprising a first suture coupled to at least two of the plurality of fasteners, and a second suture coupled to at least two of the plurality of fasteners different from the at least two of the plurality of fasteners coupled to the first suture.

18. The device of claim 1, wherein the device is reconditioned for use following at least one prior use of the device.

19. A device for reducing a size of a lumen, comprising:

an end effector having a circular trough formed around a circumference thereof for receiving tissue around a lumen and including at least one suction port for suctioning tissue into the trough, the end effector having a proximal actuator disposed in a proximal portion of the trough and a distal actuator disposed within a distal portion of the trough, the proximal and distal actuators being adapted to retain a plurality of fasteners such that the plurality of fasteners extend across the trough and opposed terminal ends of the plurality of fasteners are configured to extend into opposite sides of tissue disposed within the trough to thereby engage the tissue, and the proximal and distal actuators being rotatable to release the plurality of fasteners therefrom such that the plurality of fasteners move from an open position to a closed position to engage tissue; and at least one tissue-injuring element disposed within the trough and adapted to injure tissue.

20. The device of claim 19, wherein the trough includes at least one tissue-injuring element located within the trough and adapted to injure tissue.

21. The device of claim 19, wherein the trough includes a plurality of tissue-injuring elements spaced apart from one another within the trough.

22. The device of claim 19, further comprising a plurality of fasteners releasably disposed within the end effector and positioned in a substantially circumferential pattern, the plurality of fasteners being configured to engage tissue disposed within the trough.

23. The device of claim 22, wherein the plurality of fasteners are biased to a closed, ring-shaped configuration.

24. The device of claim 19, wherein the proximal rotatable actuator is adapted to hold a first leg of the plurality of fasteners and the distal rotatable actuator is adapted to hold a second leg of the plurality of fasteners.

25. The device of claim 24, wherein the proximal rotatable actuator is independently rotatable from the distal rotatable actuator.

26. The device of claim 19, wherein the end effector is formed on an elongate shaft having a longitudinal axis and proximal and distal ends, and the plurality of fasteners are oriented to extend along the longitudinal axis such that opposed terminal ends extend toward the proximal and distal ends of the elongate shaft.

* * * * *